(12) United States Patent
Wittkampf et al.

(10) Patent No.: US 10,166,067 B2
(45) Date of Patent: Jan. 1, 2019

(54) ABLATION CATHETER AND METHOD FOR ELECTRICALLY ISOLATING CARDIAC TISSUE

(75) Inventors: Frederik Henricus Mattheus Wittkampf, Lage Vuursche (NL); Helmert Van Wessel, Elst (NL); Richard E. Stehr, Stillwater, MN (US); Martin M. Grasse, Chicago, IL (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 821 days.

(21) Appl. No.: 13/201,052

(22) PCT Filed: Feb. 12, 2009

(86) PCT No.: PCT/EP2009/001199
§ 371 (c)(1),
(2), (4) Date: Nov. 10, 2011

(87) PCT Pub. No.: WO2010/091701
PCT Pub. Date: Aug. 19, 2010

(65) Prior Publication Data
US 2012/0053581 A1 Mar. 1, 2012

(51) Int. Cl.
*A61B 18/14* (2006.01)
*A61B 17/00* (2006.01)
(Continued)

(52) U.S. Cl.
CPC .......... *A61B 18/1492* (2013.01); *A61B 34/20* (2016.02); *A61B 2017/003* (2013.01);
(Continued)

(58) Field of Classification Search
CPC ........ A61B 18/1492; A61B 2018/1407; A61B 2018/1273; A61B 2018/1497; A61B 2018/1465; A61B 2018/1467; A61B 2018/162; A61B 19/5244; A61B 2018/1253; A61B 2018/126;
(Continued)

(56) References Cited

U.S. PATENT DOCUMENTS 5,733,323 A * 3/1998 Buck et al. .................. 607/122
6,731,981 B1 * 5/2004 Hemmingsson et al. ...... 607/13
(Continued)

FOREIGN PATENT DOCUMENTS

EP    1042990       10/2000
EP    1042990 A1 * 10/2000 ............. A61B 18/14
(Continued)

OTHER PUBLICATIONS

Scheinman, M.M. Catheter Ablation of Cardiac Arrhythmias, (1988), Cardiology, p. 2.*
(Continued)

*Primary Examiner* — Eunhwa Kim
(74) *Attorney, Agent, or Firm* — Dykema Gossett PLLC

(57) ABSTRACT

Ablation catheter comprising an elongate member with proximal and distal ends, wherein the distal end is arranged to apply a high energy electrical shock from a plurality of locations along the length of said distal end and wherein said distal end is curved. Preferably the distal end of the elongate member extends in a circle segment.

19 Claims, 8 Drawing Sheets

Figure 1:
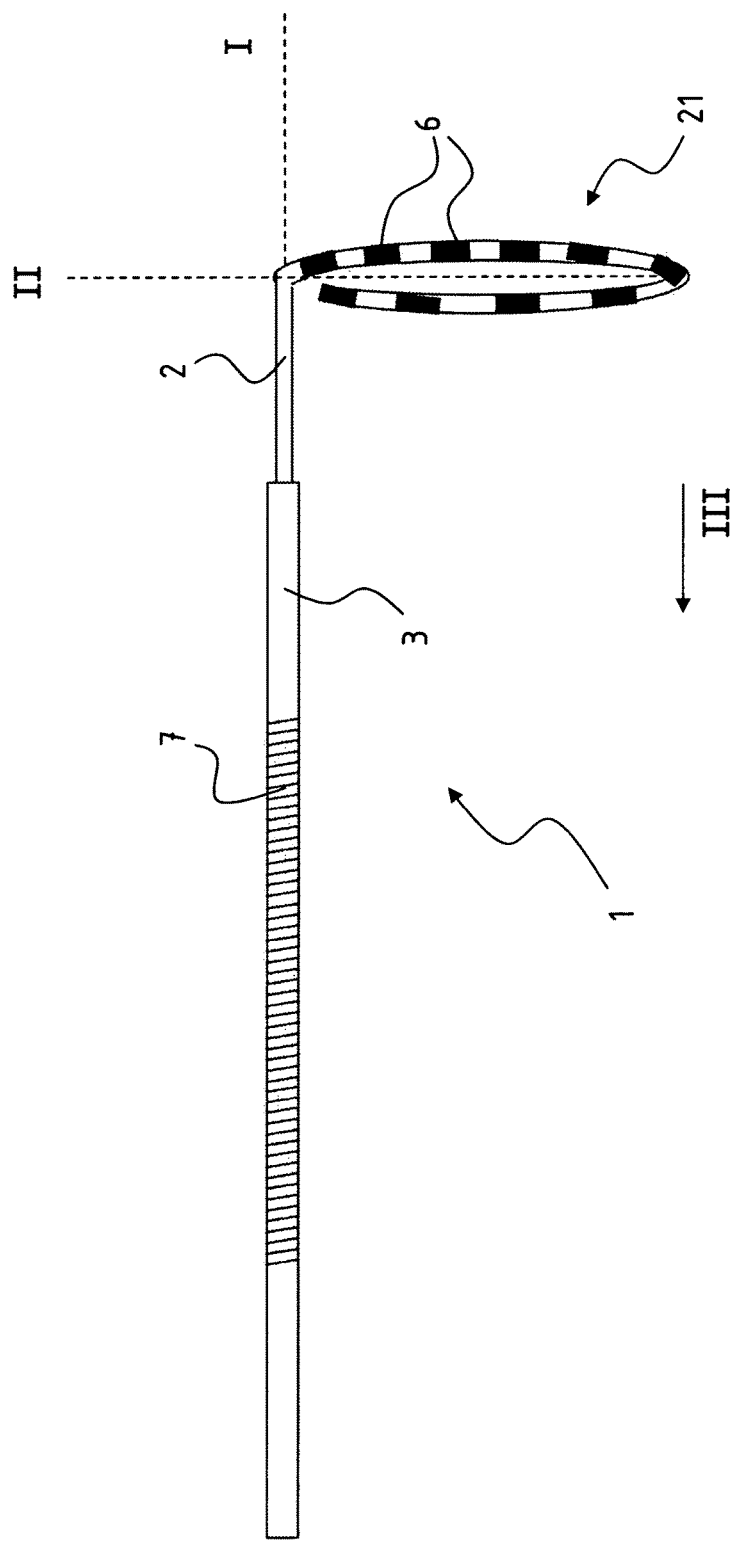

(51) Int. Cl.
   *A61B 18/00* (2006.01)
   *A61B 18/12* (2006.01)
   *A61B 18/16* (2006.01)
   *A61N 1/39* (2006.01)
   *A61B 34/20* (2016.01)

(52) U.S. Cl.
   CPC ............... *A61B 2017/00867* (2013.01); *A61B 2018/0016* (2013.01); *A61B 2018/00375* (2013.01); *A61B 2018/00761* (2013.01); *A61B 2018/00839* (2013.01); *A61B 2018/126* (2013.01); *A61B 2018/1253* (2013.01); *A61B 2018/1266* (2013.01); *A61B 2018/1273* (2013.01); *A61B 2018/1407* (2013.01); *A61B 2018/1465* (2013.01); *A61B 2018/1467* (2013.01); *A61B 2018/1475* (2013.01); *A61B 2018/1497* (2013.01); *A61B 2018/162* (2013.01); *A61N 1/395* (2013.01); *C08L 2201/12* (2013.01)

(58) Field of Classification Search
   CPC .......... A61B 2018/00375; A61B 2018/00839; A61B 2017/003; A61N 1/395
   USPC .......................................................... 606/41
   See application file for complete search history.

(56) References Cited

U.S. PATENT DOCUMENTS

| | | | |
|---|---|---|---|
| 6,936,024 B1 | 8/2005 | Houser | |
| 2002/0123747 A1 | 9/2002 | Wentzel et al. | |
| 2002/0128640 A1* | 9/2002 | Swanson | A61B 18/1492 606/32 |
| 2003/0055422 A1 | 3/2003 | Lesh | |
| 2004/0193239 A1* | 9/2004 | Falwell | A61B 18/1492 607/122 |
| 2005/0004565 A1 | 1/2005 | Vanney | |
| 2005/0159738 A1* | 7/2005 | Visram | A61B 18/1492 606/34 |
| 2005/0261672 A1* | 11/2005 | Deem | A61B 18/1492 606/41 |
| 2006/0200118 A1* | 9/2006 | Krishnan | A61B 18/1492 606/32 |
| 2008/0146918 A1* | 6/2008 | Magnin | A61B 8/0841 600/437 |
| 2010/0023004 A1* | 1/2010 | Francischelli | A61B 18/1442 606/41 |
| 2010/0179530 A1* | 7/2010 | Long | A61B 18/1206 606/33 |

FOREIGN PATENT DOCUMENTS

| | | | | |
|---|---|---|---|---|
| JP | H11216189 | 8/1999 | | |
| JP | 2003514635 | 4/2003 | | |
| WO | 1996010950 | 4/1996 | | |
| WO | WO 9610950 A1 * | 4/1996 | ............... | A61B 5/04 |
| WO | 2000051511 | 9/2000 | | |
| WO | 2004039273 | 5/2004 | | |
| WO | WO 2004039273 A2 * | 5/2004 | ............. | A61B 18/14 |
| WO | 2006058251 | 6/2006 | | |

OTHER PUBLICATIONS

Scheinman, M.M., Catheter Ablation of Cardiac Arrhythmias: Basic Bioelectrical Effects and Clinical Indications, 1988, vol. 78, p. 1-36.*

Huang et al. Comparison of Catheter Ablation Using Radiofrequency Versus Direct Current Energy: Biophysical, Electrophysiologic and Pathologic Observations, 1991: 1091-7.*

International Search Report for International Application No. PCT/EP2009/001199, dated Oct. 19, 2011.

* cited by examiner

ABLATION CATHETER AND METHOD FOR ELECTICALLY ISOLATING CARDIAC TISSUE

The present invention relates to an ablation catheter and method for electrically isolating cardiac tissue. More in particular, the invention relates to a method for complete circular electrical isolation of the pulmonary vein ostia at their entrance to the left atrium.

Pulmonary veins are known sources or atrial arrhythmias and atrial fibrillation and the borders between the mouth (ostium) of the pulmonary veins and the left atrium (pulmonary vein antrum) are known areas with slow electrical conduction that may be part of the substrate that maintains atrial fibrillation once it has started. Complete electrical pulmonary vein antrum isolation may cure the disease in approximately 75% of patients. Electrical isolation through cardiac muscle can be achieved by causing permanent tissue damage that causes replacement of cardiac tissue by fibrotic tissue. In contrast to cardiac muscle, fibrotic tissue blocks a propagating electrical wave front and thus causes electrical isolation.

At present, various techniques are used for pulmonary vein antrum isolation. Such techniques include ablation by heating, for instance radiofrequency ablations or using ultrasound or laser energy, and cryo ablation.

The abovementioned techniques all have their disadvantageous and drawbacks. Some are very time consuming, some require complex technology and very expensive, thick poorly steerable catheters and some often only cause transient electrical isolation with late recurrences. Some are risky because of the possible formation of blood clots or may cause esophageal fistulae, an often deadly leak between left atrial cavity and the esophagus due to damage to the wall of the esophagus which is very close to the posterior left atrial wall.

It is an object of the invention to provide in a safe, efficient, and/or easy to use catheter for use in an ablation procedure, specifically for complete circular electrical isolation of the pulmonary vein ostia at their entrance to the left atrium.

In order to accomplish that objective, the ablation catheter according to the invention comprises an elongate member with proximal and distal ends, wherein the distal end comprises at least one electrode and is arranged to apply a high energy electrical shock from a plurality of locations along the length of said distal end and wherein said distal end is curved. The curved distal end of the elongate member provides a good contact between the tissue to be treated and the electrode. Preferably the curvature of the distal end of the elongate member is adapted to the surface curvature of the tissue to be treated such that the curved distal end is substantially complementary to the surface of the tissue to be treated.

The present invention is based on the discovery that by using a DC ablation technique with a plurality of shock delivery locations which, due to the curvature of the distal end, are placed in close contact with the tissue to be treated, it is possible to efficiently isolate an area of tissue. The locations extend along a path on the tissue and by applying a sufficiently high electrical shock to the distal end, the tissue areas contacting the delivery locations become permanently nonconductive.

Furthermore, by using a plurality of shock delivery locations in close contact with the tissue to be treated, the need for repositioning the catheter multiple times for creating an electrical isolation between two areas of cardiac tissue is reduced. With the device according to the invention, a relative long length of cardiac tissue can be treated in a single operation, reducing the procedure time.

The term high energy electrical shock as used herein should be interpreted as a shock applied during approximately 5 ms of between 200 and 500 Joule, preferably between 250 and 400 Joule and more preferably of approximately 350 Joule. By applying the shock from a plurality of locations along the distal end, the energy is distributed over said length, limiting the energy per unit of length. The risk of explosions and sparking associated with DC ablation near the electrode is hereby reduced.

In order to be able to deliver shocks at the distal end of the catheter, the elongate member is provided with suitable conducting means for conducting high energy electrical current from the proximal end of the elongate member to the distal end provided with the electrode. Preferably the guiding means comprise a guiding core provided in the elongate member.

According to a preferred embodiment of the invention, the distal end of the elongate member extends in a circle segment. Since cardiac tissue surfaces are normally curved, providing a distal end with a substantially complementary shape in the form of a circle segment enhances the contact between the distal end provided with the at least one electrode and the tissue. The circle segment for instance allows a close fit of the distal end to at least a part of the cross section of the ostia of the pulmonary veins. Preferably the distal end of the elongate member extends substantially circular. The distal end is hereby loop shaped. Using a distal end extending in a circle segment or loop, a tubular tissue surface, for instance a vein, can be treated along a cross section in a single operation. By providing a nonconductive cross section in said tubular tissue, the tissue areas extending adjacent said nonconductive tissue are isolated. Preferably the radius of the circle segment is between 5 to 25 mm, preferably between 10 and 20 mm.

More preferably the curvature of the distal end is adjustable, more specifically the diameter of the circle segment is adjustable. This allows a custom fit of the distal end of the elongate member to the surface of the tissue to be treated, regardless of the diameter or the curvature of said tissue.

According to a further preferred embodiment of the invention the curved distal end of the elongate member extends in a plane under an angle with respect to the axis of the elongate member. For instance when treating an inner wall of a vessel, the catheter is advanced along the longitudinal axis of said vessel. When the electrode on the distal end extends in a plane under an angle with the axis of the elongate member, it is possible to efficiently contact the wall of said vessel at substantially any longitudinal location in said vessel. Preferably the curved distal end of the elongate member extends in a plane substantially perpendicular to the axis of the elongate member.

It is advantageously when the plane wherein the distal end extends is adjustable. A length proximal to the distal end of the elongate member is hereto preferably steerable. Using this steerable end, it is possible to adjust the orientation of the plane wherein the curved distal end extends to the surface of the tissue to be treated. Preferably the elongate member is allowed to bend on a location proximal to the curvature of said distal end. This allows an efficient adjustment of the plane wherein said distal end extends.

According to a first preferred embodiment of the ablation catheter according to the invention the distal end of the elongate member comprises a plurality of electrodes extending at different locations along the length of said distal end.

The shock delivery locations on the distal end are in this embodiment formed by separate electrodes. Preferably the electrodes extend at a mutual distance of between 3 and 12 mm, preferably at a distance of approximately 5 mm. A small mutual distance increases the homogeneous energy transfer the tissue and it was discovered that this results in a closed path of electrically nonconductive tissue when treated. Preferably, the electrodes extend in a circle segment at substantially equal arc distances, allowing an efficient isolation of tissue in for instance a vessel.

According to a further preferred embodiment of the invention the distal end comprises between 5 and 24 electrodes, preferably between 8 and 16 electrodes and more preferably the distal end comprises 10 electrodes. It was found that using ten electrodes, an optimal isolation of a vessel, for instance a pulmonary vein, can be achieved.

According to a further preferred embodiment the electrodes have the same polarity. This allows an efficient distribution of the electrical energy from the electrodes provided on the distal end to the tissue to be treated.

It is furthermore advantageously that when the electrodes extend in a circle segment, or more preferably in a circle, the radial outwardly distribution of the electrical energy is enhanced. Since the electrodes preferably engage the tissue with their surfaces facing radially outwardly with respect to the circle segment, the majority of the electrical energy is transferred to the tissue. It is furthermore advantageously when the electrodes comprise substantially smoothed surfaces, i.e. without any sharp edges. This prevents unwanted current concentrations around the electrodes.

According to a further preferred embodiment of the invention at least two adjacent electrodes are arranged to apply shocks with different voltages. Preferably the voltage of the applied shock alternates between adjacent electrodes. This allows a radial outwardly distribution of the electrical energy due the same polarity used for each of the electrodes, combined with a flow of electrical energy between two adjacent electrodes with different voltages. When at least a part of the electrical energy flows between the electrodes, substantially all the tissue extending between said electrodes is subjected to said electrical energy, enhancing the isolating action.

According to a further preferred embodiment of the invention the elongate member comprises conducting means arranged to separately conduct high electrical current to each of the electrodes from the proximal end to the distal end. This reduces the chance of high energy concentration near any of the individual electrodes in case of electrode malfunctions. Each of the electrodes is preferably fed separately using a suitable power source known in the art.

According to a second preferred embodiment of the ablation catheter according to the invention the elongate member comprises one electrode extending over substantially the whole length of the curved distal end. In this embodiment, the shock delivery locations are formed by a single elongate electrode. Preferably said electrode allows bending of the distal end, allowing adjustment of the curvature or orientation of the distal end. More preferably, the electrode comprises a coil. A coil electrode is flexible and allows a curved distal end. Furthermore, using a coil enhances the steering capabilities of the distal end, for instance to adjust the curvature of said end.

According to a further preferred embodiment of the invention the elongate member is moveable between a first position wherein the elongate member extends substantially rectilinear and a second position wherein the distal end of the elongate member is curved. The straight orientation of the distal end in the first position allows an efficient advancement of the catheter through for instance a sheath into the heart. When arriving at the tissue to be treated, the elongate member can be moved to the second position wherein the distal end is curved and preferably extends in a circle segment.

When use is made of sheath for advancing the elongate member though the vasculature, the elongate member can be advanced through the sheath when the sheath is in place. The sheath extends coaxial with respect to the elongate member and encloses the elongate member, preventing deflection of the distal end in the first position. Preferably, the distal end of the elongate member is hereto manufactured from a deflectable material. More preferably the distal end comprises shape memory. Advancing the elongate member out of the sheath will then automatically result in the movement from the first to the second position.

It is possible to use an external electrode as indifferent electrode, for instance an electrode applied on the skin of the patient. This however results in high skeletal muscle activity when delivering the shocks. According to a further preferred embodiment of the invention the catheter further comprises an indifferent electrode extending proximal to the electrode. This significantly decreases the influence of the electrical shocks on the neighbouring tissue, for instance skeletal muscles. Furthermore, an integral indifferent electrode results in a compact composition of the catheter according to the invention. Preferably the indifferent electrode comprises a coil and more preferably the coil extends coaxial to the elongate member. Preferably the indifferent electrode extends a distance of between 3 and 10 cm from the most proximal shock delivery location, and more preferably the indifferent electrode extends a distance of approximately 5 cm from the most proximal shock delivery location.

Is it advantageously when the catheter is provided with a sheath, wherein the sheath is provided with the indifferent electrode. When using a sheath, preferably a steerable sheath, the distal end of the sheath is usually advanced in the left atrium. By subsequently advancing the elongate member through the sheath, access to the left atrium is provided for the catheter according to the invention. When the distal end of the sheath is provided with the indifferent electrode, preferably a coil, the indifferent electrode preferably extends at a location with little skeletal muscle tissue in use, for instance in the right atrium or the inferior vena cava.

It is furthermore advantageously to use a localization system known in the art to localize the catheter in the heart. The one electrode or the plurality of electrodes provided on the distal end can then be localized in the heart. Such a system furthermore allows an accurate mapping of the heart, allowing an accurate deployment of the curved distal end on the heart tissue to be treated.

According to a further preferred embodiment of the invention, the catheter is arranged to apply a high energy shock in dependence of the heart rhythm. This allows cardioversion, i.e. ending atrium fibrillation. Preferably, the catheter is arranged to apply the shock outside the vulnerable phases in the heart rhythm of both the atrium and the ventricle. This enables cardioversion without inducing ventricle fibrillation. Preferably the electrode, or more preferably at least one of the plurality of electrodes, on the distal end is arranged to monitor the heart rhythm.

Preferably, the catheter of the invention is provided with a suitable connector at the proximal end to connect the catheter to measurement means known in the art for monitoring the heart rhythm.

Even more preferably, the indifferent electrode is located on the elongate member such that said electrode at least partially extends in another chamber, preferably in the right atrium, while the electrode on the distal end extends near the left atrium. This enhances the cardioversion since both poles, the indifferent electrode and the electrode on the distal end, extend in different chambers.

The invention furthermore relates to a method for electrically isolating cardiac tissue, comprising the steps of:
   providing an ablation catheter comprising an elongate member with proximal and distal ends, wherein the distal end is provided with at least one electrode and is arranged to apply a high energy electrical shock from a plurality of locations along the length of said distal end and wherein said distal end is curved;
   advancing the ablation catheter to the cardiac tissue;
   contacting the distal end with the cardiac tissue, and;
   applying a high energy electrical shock from the plurality of locations along said length of the distal end to the cardiac tissue.

With the method according to the invention, a plurality of shock delivery locations is placed in close contact with the tissue to be treated wherein at least two locations extend at a mutual distance. The curvature of the distal end provided with the at least one electrode provides such close contact. Preferably the curvature of the distal end of the elongate member is complementary to the surface of the tissue to be treated.

With the electrode extending in a path on the tissue, a high energy electrical shock is delivered to the distal end of the elongate member from the plurality of shock delivery locations of the electrode. As a result, the tissue in the neighbouring area of the electrode is made nonconductive. It will be appreciated that with the method according to the invention an efficient method for electrically isolating an area of tissue is provided.

Preferably the step of applying a high energy electrical shock comprises applying a shock during a predetermined period of time of between 200 and 500 Joule, preferably between 250 and 400 Joule and more preferably of approximately 350 Joule. It was found that 350 Joule is enough for complete and permanent electrical isolation of the cardiac tissue. Preferably the predetermined period of time is smaller than 10 ms, more preferably smaller than 5 ms and even more preferably the period of time is approximately 1 ms. Since the shock is delivered from a plurality of locations during a short period of time, the energy per unit of length is sufficiently small to prevent sparking and bubble forming associated with traditional direct current ablation.

According to a preferred embodiment the distal end comprises a plurality of electrodes, wherein the electrodes have the same polarity. In this embodiment the shock delivery locations are formed by at least two separate electrodes at a mutual distance. Applying a shock from a plurality of electrodes with the same polarity allows an optimal distribution of the electrical energy. Preferably, applying a high energy electrical shock comprises simultaneously applying a shock from the plurality of electrodes. This furthermore enhances the distribution of the electrical energy to the tissue to be treated.

It is furthermore advantageously when applying a high energy electrical shock comprises applying shocks with different voltages from at least two adjacent electrodes along the length of the distal end. The difference in voltage between two adjacent electrodes provides a flow of electrical current between said electrodes. Next to the flow outwardly due to the same polarity of the electrodes, at least a part of the electrical energy flows between adjacent electrodes. This ensures that substantially all tissue extending between the electrodes is subjected to electrical energy, resulting in a closed path of treated tissue. Preferably the voltages of the shock applied from the different electrodes alternates.

According to another embodiment the elongate member comprises one electrode extending along substantially the whole length of the distal end. By contacting the surface of the tissue with the elongate electrode, for instance a coil, a closed path is formed. The shock is then applied from a plurality of locations along the length of said electrode to the tissue.

According to a preferred embodiment the step of contacting the cardiac tissue comprises contacting the tissue along a path, wherein applying the shock comprises forming a closed path of electrically non-conducting tissue. The electrode(s) extend(s) along a path on the tissue prior to the application of the shock. In case a plurality of electrodes is used, the distance between the electrodes is sufficiently small such that al tissue extending between two adjacent electrodes is subjected to sufficient electrical energy, resulting in a closed path of non-conductive tissue.

Preferably the step of contacting the cardiac tissue comprises adjusting the curvature of the distal end of elongate member to the surface of the cardiac tissue to be isolated. Using a steerable distal end, the shock delivery locations along the distal end, for instance the plurality of electrodes, can be placed in close proximity with the tissue, resulting in a more efficient energy transfer from the at least one electrode to the tissue. Preferably the distal end of the elongate member extends in a circle segment, wherein the step of contacting comprises adjusting the diameter of the circle segment to the surface of the cardiac tissue. The diameter of the circle segment is adjusted to the diameter of the tissue to be treated, for instance to the inner diameter of a vessel.

It is also advantageously when the step of contacting comprises adjusting the plane wherein the curved segment extends to the surface of the cardiac tissue. When the surface of the tissue extends under an angle with respect to for instance the longitudinal axis of the elongate member, it is possible to adjust the plane of the electrode(s) to enable a close fit of the distal end of the elongate member to said surface.

Being able to adjust both the diameter of the circle segment and the angle of the circle segment with respect to the axis of the elongate member, it is possible to ensure a close contact between the electrode(s) and the tissue.

According to a further preferred embodiment of the invention the catheter comprises a sheath, wherein advancing the catheter through the vasculature comprises advancing the catheter through the sheath, wherein the elongate member is moveable between a first position wherein the elongate member extends substantially rectilinear and a second position wherein the distal end of the elongate member is curved, wherein the elongate member moves from the first to the second position by advancing the elongate member out of the sheath. In the first position the elongate member is restricted to deflect by the sheath enabling easy advancement of the elongate member through the sheath. When moving the elongate member distally out of the sheath the elongate member will move towards the second position and enables a close fit of the electrodes to the tissue.

According to a further preferred embodiment of the invention, applying a high electrical current comprises using an electrode provided on the catheter as indifferent electrode. Preferably the electrode comprises a coil. This results in a compact composition. Furthermore, external indifferent electrodes, for instance a skin patch, are associated with negative effects for the patients. In the case of using an external electrode, the skeletal muscle contracts heavily during the shock and it often causes displacement of the patient on the catheterization table. Using an indifferent electrode provided on the catheter minimizes this problem.

According to a further preferred embodiment of the invention the cardiac tissue comprises pulmonary vein ostia, preferably pulmonary vein ostia near the entrance to the left atrium. Pulmonary veins are known sources of atrial arrhythmias and atrial fibrillation. With the method according to the invention there is provided an efficient method for isolating said veins from the atrium. Preferably contacting the cardiac tissue comprises contacting the ostia of the pulmonary vein with the distal end along a cross section of the vein. In this way a cross section of the pulmonary vein is made nonconductive, separating the tissue areas extending adjacent the nonconductive border.

More preferably advancing to the cardiac tissue comprises advancing the sheath provided with an indifferent electrode in the vicinity of the distal end extending in said atrium. Providing the indifferent electrode, for instance in the form of a coil, on the sheath allows a close relationship between the electrode(s) on the distal end and the indifferent electrode, minimizing the influence of the shock on the neighbouring tissue. Preferably the indifferent electrode is located in use at a location with little skeletal muscle tissue, for instance the right atrium or the inferior vena cava.

A further preferred embodiment of the invention further comprises the step of monitoring the heart rhythm and applying the shock in dependence of said heart rhythm. The ECG is measured at least prior to applying the shock. The ECG, and in particular the P-wave of said ECG, is preferably measured using the electrode provided on the distal end of the catheter according to the invention. It is however also possible to use other measuring methods known to the person skilled in the art. Measuring the P-wave using external measuring methods is however difficult in some conditions. Measuring said P-wave using internal electrodes, for instance an electrode provided on the catheter or a separate catheter provided in the heart, allows a more reliable measurement.

Preferably the shock is applied at a predetermined time in the heart rhythm outside the vulnerable phases of both the atria and the ventricles. Normally only the vulnerable phase of the ventricles is considered to prevent ventricular fibrillation. According to the method of the invention, the energy shock is also applied outside the vulnerable phase of the atrium, preventing atrium fibrillation to occur when applying the shock. This furthermore allows efficient cardioversion. Preferably, the energy shock is applied on or before the QRS-complex of the ECG.

Figure 2:
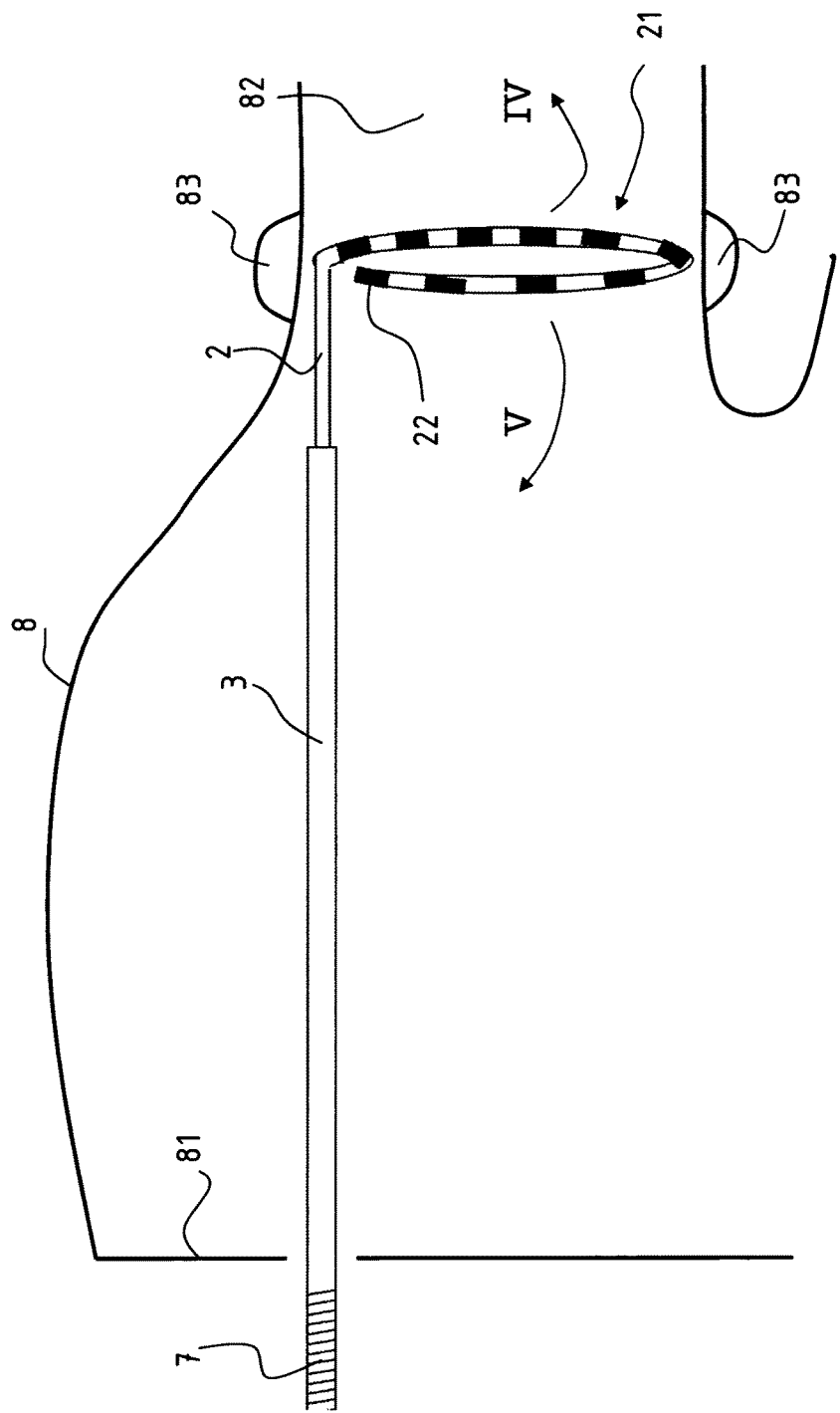
Figure 4:
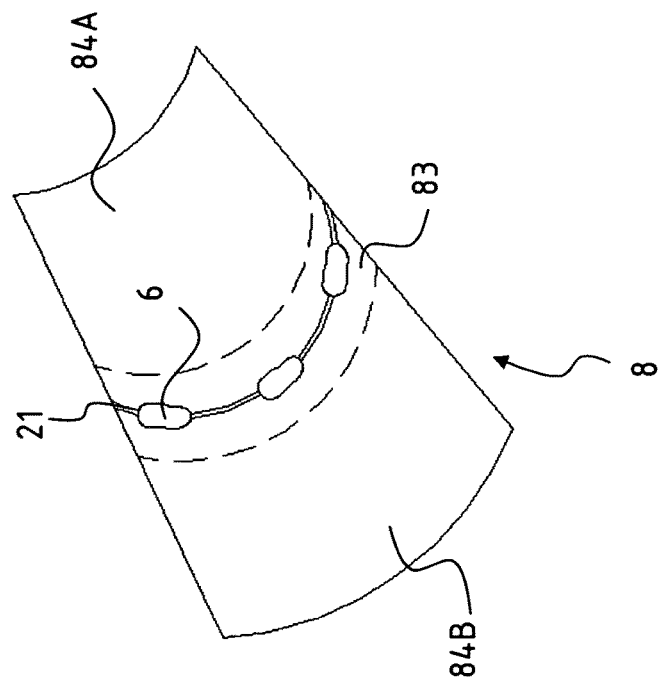
Figure 3:
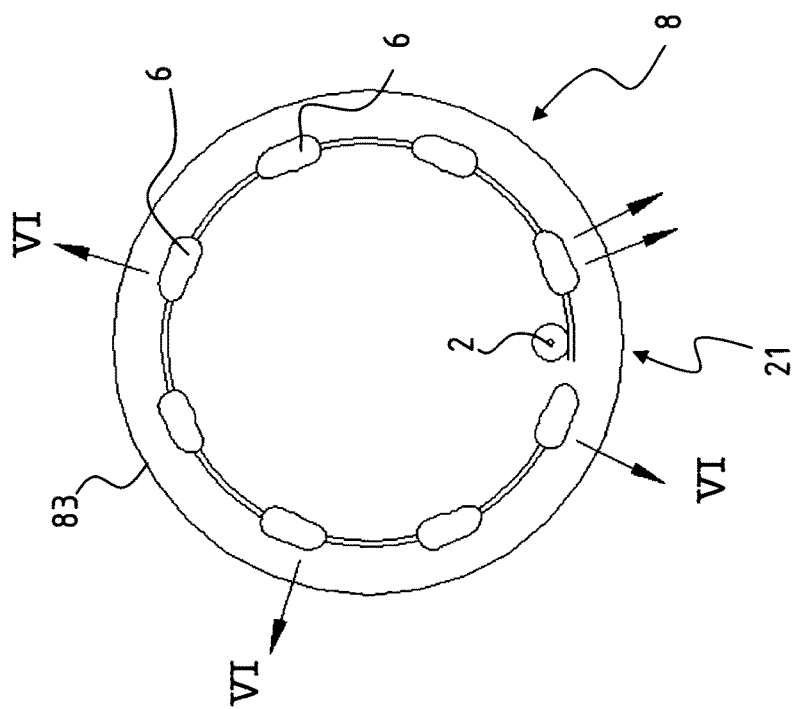
Figure 5:
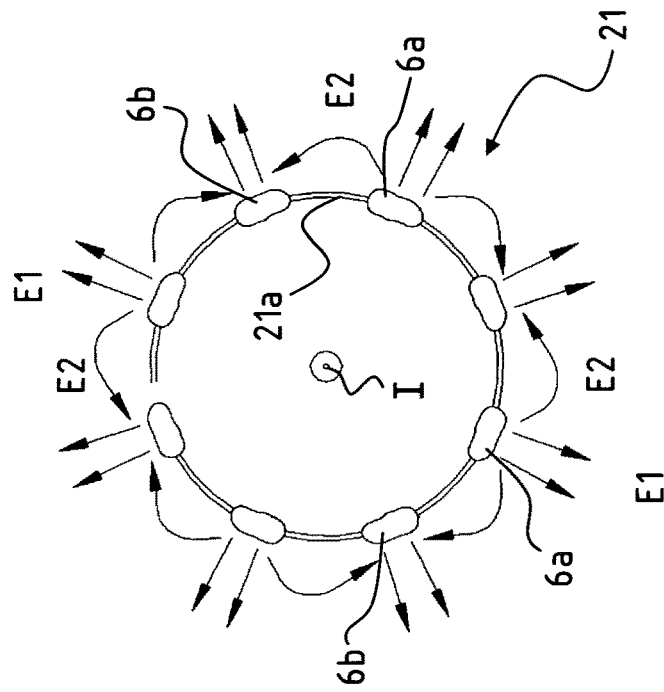

The present invention is further illustrated by the following Figures, which show a preferred embodiment of the device according to the invention, and are not intended to limit the scope of the invention in any way, wherein:

FIG. 1 schematically shows a ablation catheter according to the invention;

FIG. 2 schematically shows the catheter in the left atrium;

FIG. 3 schematically shown the catheter in a vessel in cross section;

FIG. 4 schematically shows a curved tissue area in perspective;

FIG. 5 schematically shows the distribution of the electrical energy from the electrodes.

Figure 6:
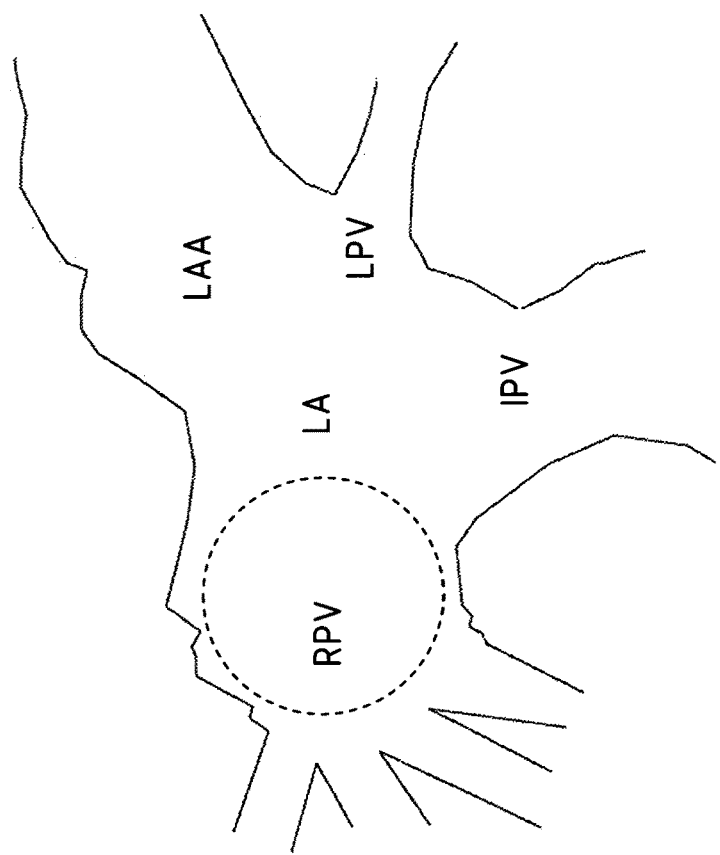
Figure 7A:
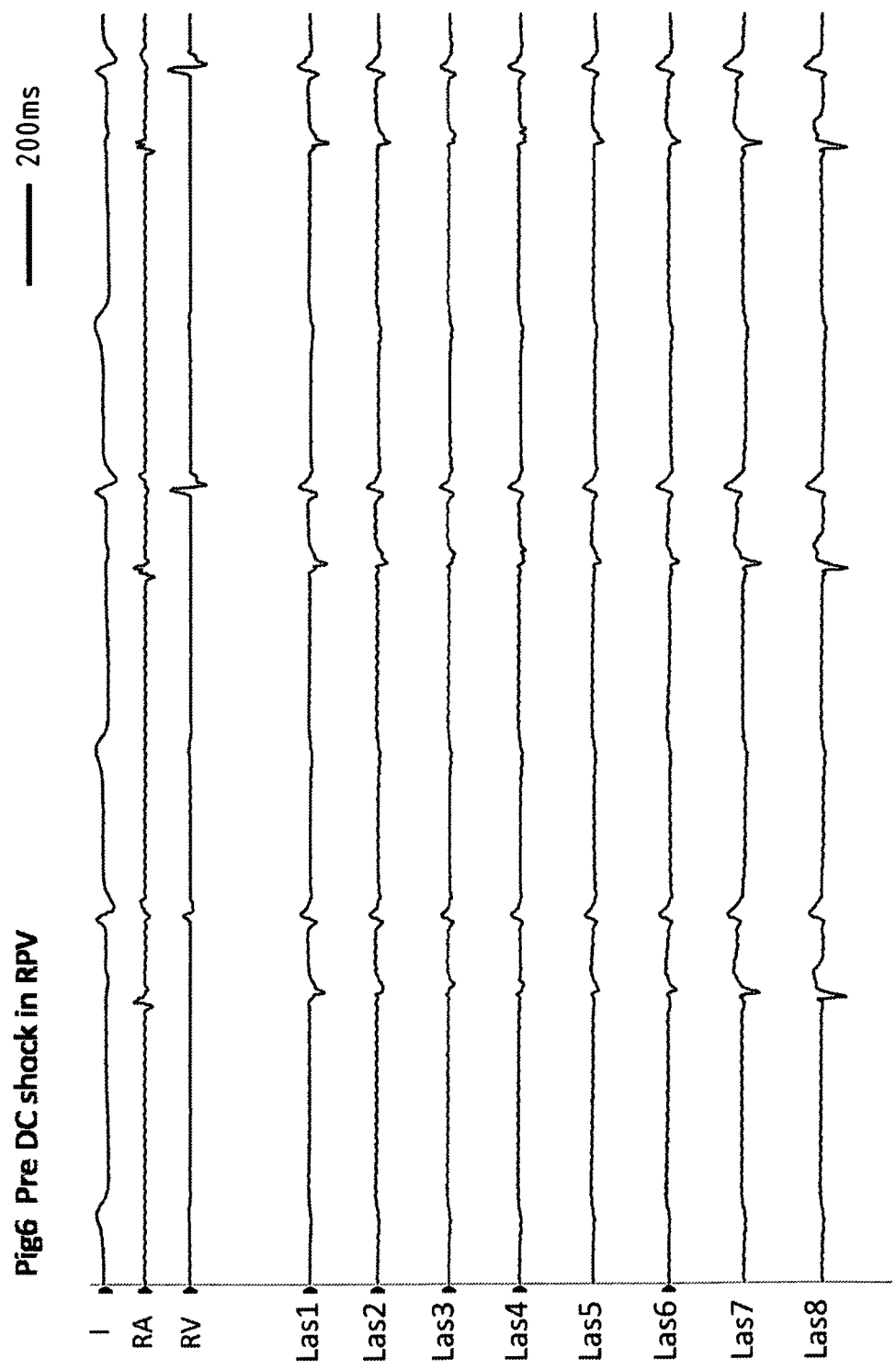
Figure 7B:
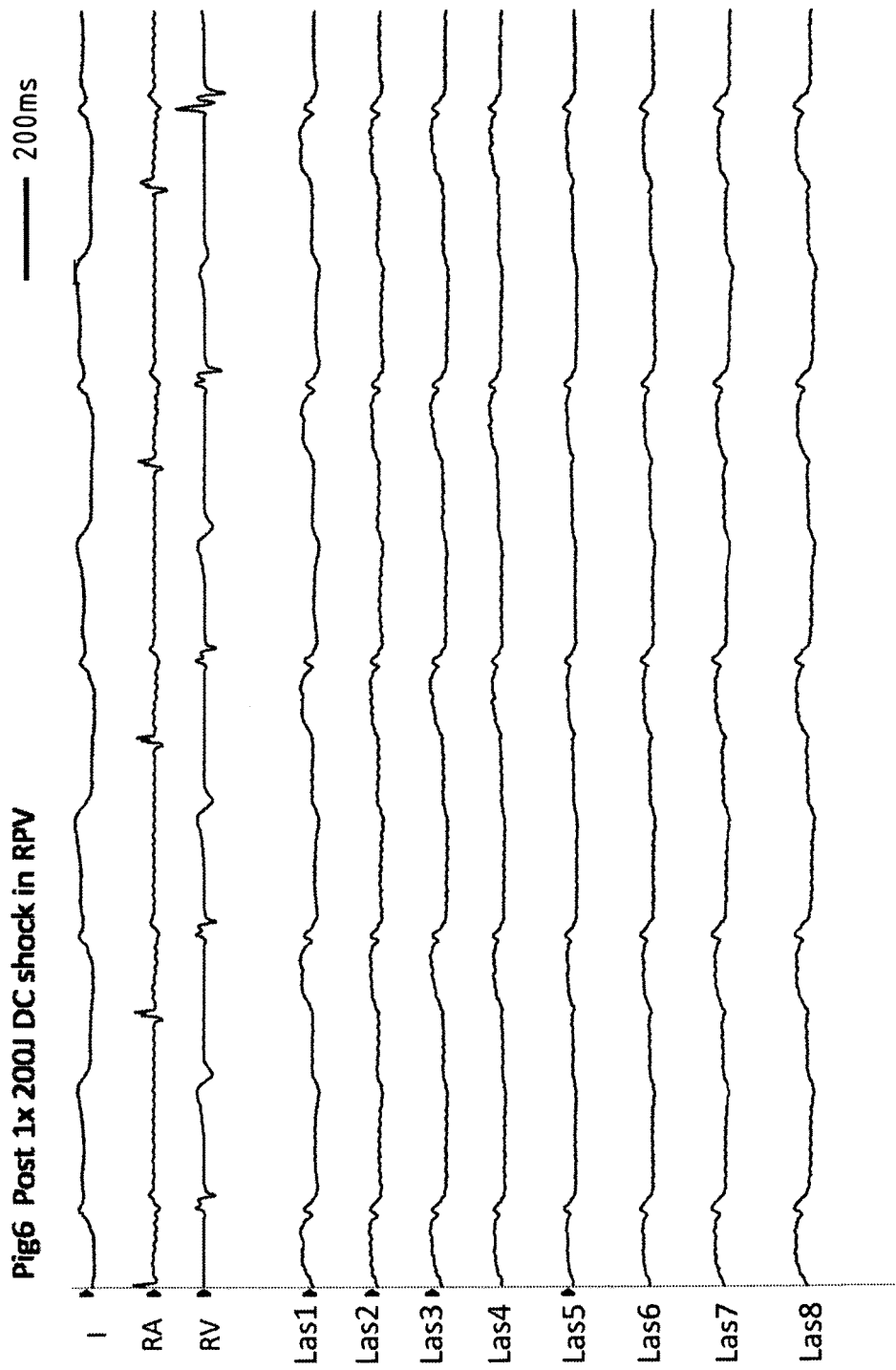
Figure 8A:
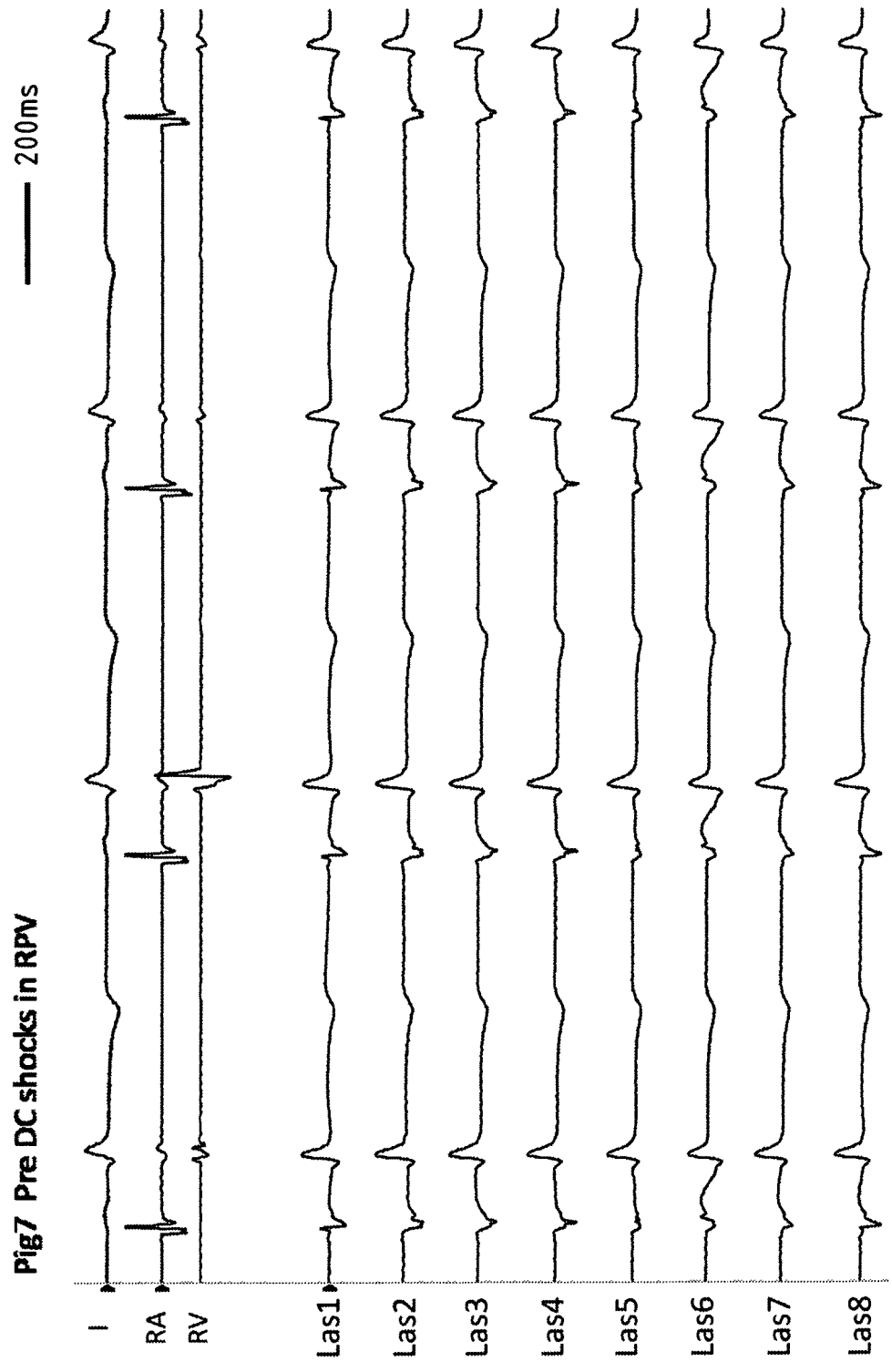
Figure 8B:
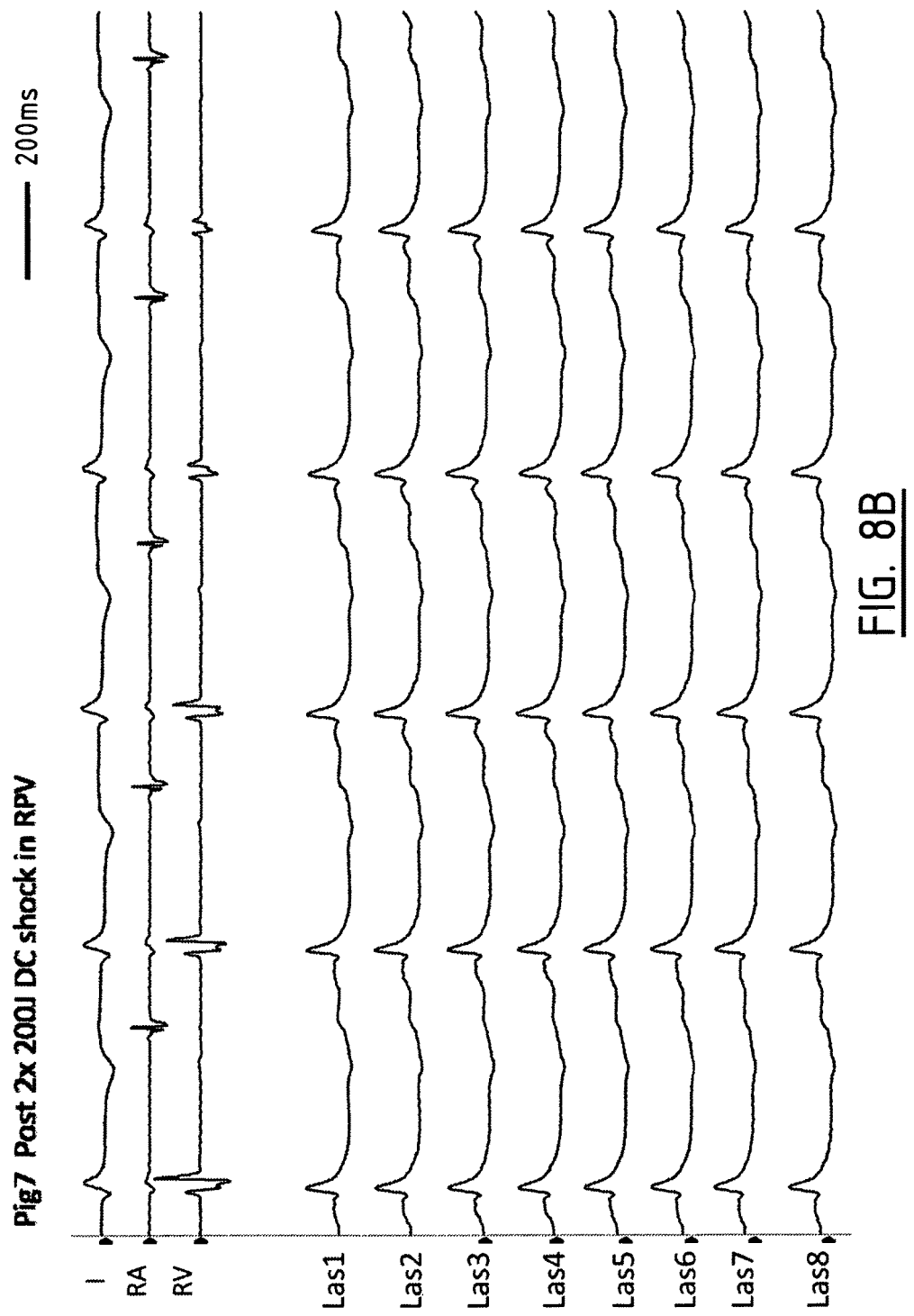

FIG. 6 schematically shows a heart of a pig, and;

FIGS. 7 and 8 show the results of a test conducted on a pig.

In FIG. 1 a catheter 1 according to the invention is shown. The catheter 1 comprises an elongate member 2 with a proximal end (not shown) and a distal end 21. The distal end 21 of the elongate member is curved. In this example the distal end 21 extends in a circle segment, wherein the distal end 21 forms a loop or a lasso. The distal end 21 extends in a plane II under an angle with respect to the longitudinal axis I of the elongate member 2. The distal end 21 is provided with a plurality of electrodes 6, in this case ten. The electrodes 6 extend on mutually distances of 5 mm.

The distal end 21 of elongate member 2 is steerable which allows the practitioner to adjust the plane II of the electrodes 6. This facilitates the placement of the electrodes on the tissue to be treated as will be explained in more detail below. Also shown is a steerable sheath 3, which allows an efficient advancement of the catheter 1 through the vasculature. In this embodiment the sheath 3 is provided with an indifferent electrode in the form of a coil 7. The coil 7 is disposed coaxially to the sheath.

The distal end 21 forming the loop is preferably manufactured from a deflectable material. When the elongate member 2 is drawn into the sheath 3 in a direction indicated with III, the distal end 21 will deform such that the distal end 21 will extend substantially rectilinear. In this first position the distal end 21 is contained in the sheath 3. This results in a compact composition. In the first position, the elongate member 2 can be advanced through the sheath 3 to the tissue to be treated. When the catheter 1 is advanced to the tissue, the elongate member 21 is advanced out of the sheath 3, and the distal end 21 deflects back to the second position, as shown in FIG. 1.

In FIG. 2 the catheter 1 is shown in place in the left atrium 8 of the heart. The sheath 3 advanced through the septum 81. The coil 7 hereby extends in the right atrium. In order to isolate a tissue area from the pulmonary vein 82, the distal end 21 of the elongate member 2 is advanced in said vein 82 such that the electrodes 6 contact the wall along a cross section of said vein 82.

In order to facilitate the placement of the electrodes 6 onto the wall of the vein 82, the most distal end 22 is steerable, allowing the plane of the electrodes 6, indicated with II in FIG. 1, to be adjusted in directions indicated with V and VI.

Using the steerable most distal end 22 it is also possible to adjust the diameter of the circle segment wherein the electrodes 6 extend, as is shown schematically in FIG. 3. When the distal end 21 is advanced in a vein 82 it is possible that the electrodes 6 do not contact the tissue closely, as the case in FIG. 3. In order to achieve a close fit of the distal end 21 provided with the electrodes 6 to the wall, the diameter can be adjusted. The electrodes 6 are moved in a direction indicated with VI to achieve a close contact between the wall of the vein 82 and the electrodes 6.

As is shown in FIG. 3, the distal end 21 provided with the electrodes 6 forms a closed loop over a cross section of the vein 82. The electrodes 6 extend over a closed loop over the inner wall of the vein, isolating the tissue areas extending adjacent the distal end 21 (below and above the plane of FIG. 3).

Referring back to FIG. 2, when the electrodes are placed in close contact with the tissue 83 to be treated, a high energy electrical shock of approximately 350 Joule is applied to the electrodes 6 during approximately 5 ms. Since ten electrodes 6 are used, each of the electrodes 6 delivers a shock of approximately 35 Joule. It was discovered that this is sufficiently to permanently make the tissue 83 extending in the proximity of the electrode nonconductive, isolating the vein 82 from the left atrium 8.

In order to achieve a good isolation between the tissue areas, the distance between two electrodes 6 is sufficiently small to ensure that all tissue 83 extending between electrodes 6 is subjected to electrical energy sufficiently high to induce non-conductivity. This ensures a proper isolation.

As an example, a curved surface of tissue 8 is shown in FIG. 4. In order to provide close contact between the electrodes 6 and the tissue 83 to be treated, the distal end 21 is curved complementary to the curvature of the tissue 8. All of the electrodes 6 shown therefore make contact with the tissue 83. Due to the application of the shock through the electrodes 6, the tissue indicated with 83 is made nonconductive. This isolates the tissue indicated with 84a from the tissue indicated with 84b.

To enhance the distribution of the electrical energy from the electrodes 6 to the tissue, the polarity of all the electrodes 6 is the same. Furthermore, the catheter 1 is arranged to synchronously deliver a shock from the electrodes 6. Each of the electrodes is hereto provided with a separate power source known in the art. This results in a radially outwardly distribution of the electrical energy indicated with E1 in FIG. 5. The term radial must be interpreted with respect to the longitudinal axis I of the elongate member in the case where the distal end 21 extends in the plane II perpendicular to the axis I as shown in FIGS. 1 and 2.

In FIG. 5, the electrodes 6 are arranged to deliver a shock of an alternating voltage between the electrodes. The electrodes 6a are arranged to deliver a shock with a voltage of 3500V, while the electrodes 6b are arranged to deliver a shock of 3000V. This difference in voltage between adjacent electrodes results in a flow of electrical energy E2 between the adjacent electrodes 6a and 6b. This ensures that tissue extending near the region 21a between the electrodes 6 is also sufficiently subjected to electrical energy E2.

The present invention is not limited to the embodiment shown, but extends also to other embodiments falling within the scope of the appended claims. It will be understood that although an embodiment is shown using a plurality of electrodes, it is also possible to use one single elongate electrode which can be placed in close contact with the tissue to be treated.

EXAMPLE

The invention will now further be elucidated using an example.

In FIG. 6 a sketch of the reconstructed geometry of the left atrium of a pig is shown. The left atrium (LA), three pulmonary vein ostia (RPV, IPV and LPV) and part of the left atrial appendage (LAA) are shown. DC ablations according to the invention were performed in the ostia of the right RPV and left pulmonary veins LPV.

The intention of the ablation procedure is to destroy all vital atrial myocardium inside the ostium of the pulmonary veins. Such destruction translates into a dramatic reduction of local electrograms, measured using endocardial catheters.

FIG. 7A shows an electrocardiogram I of the pig's heart prior to ablation. RA and RV are electrograms of the right atrium and the right ventricle. La1-8 are recordings from a lasso catheter in various positions in the atrium.

A catheter according to the invention had been placed inside the ostium of the right pulmonary vein ostium in four different positions. One of the positions is schematically drawn using a dotted line in FIG. 6. For each position, a DC shock of 200 Joule had been delivered via the ten electrodes of that catheter (20 Joule per electrode). After those shocks, the complete ostium of the right pulmonary vein only shows very small electrogram amplitudes as can be seen from FIG. 7B, indicating the electrically active atrial tissue/muscle has been destroyed by the shocks.

FIG. 8A are the pre-recordings similar to the recordings shown in FIG. 7A for a second pig. In this case, two subsequent shocks of 200 J were applied to the tissue. Also here, as can be seen from FIG. 7B, almost all atrial signals have disappeared, indicating that a lesion has been created in the ostium.

The invention claimed is:

1. A method for electrically isolating cardiac tissue, comprising the steps of:
providing an ablation catheter comprising an elongate member with proximal and distal ends, wherein the distal end comprises a plurality of electrodes and is configured to apply a high energy electrical shock of between 200 and 500 Joule across a plurality of locations along the length of said distal end, the high energy electrical shock distributed across the plurality of locations along the length, and wherein said distal end is curved and each of the plurality of electrodes delivers a shock sufficient for ablation of cardiac tissue;
advancing the ablation catheter to the cardiac tissue;
contacting the distal end with the cardiac tissue;
monitoring a heart rhythm and applying the high energy electrical shock in dependence of said heart rhythm, wherein the high energy electrical shock is applied at a predetermined time in the heart rhythm on or before the QRS-complex of the heart rhythm and outside of vulnerable phases of both atria and ventricles of the cardiac tissue, and;
applying the high energy electrical shock during a predetermined period of time less than 10 ms from each of the plurality of locations along said length of the distal end to the cardiac tissue.

2. The method according to claim 1, wherein the distal end comprises the plurality of electrodes, wherein the plurality of electrodes have the same polarity.

3. The method according to claim 2, wherein applying the high energy electrical shock comprises applying shocks with different voltages from at least two adjacent electrodes of the plurality of electrodes along the length of the distal end.

4. The method according to claim 2, wherein applying the high energy electrical shock comprises simultaneously applying a shock from the plurality of electrodes.

5. The method according to claim 1, wherein the step of contacting the cardiac tissue comprises contacting the distal end with the cardiac tissue along a path, wherein applying the high energy electrical shock comprises forming a closed path of electrically non-conducting tissue.

6. The method according to claim 1, wherein the step of contacting the cardiac tissue comprises adjusting the curvature of the distal end of the elongate member to a surface of the cardiac tissue to be isolated.

7. The method according to claim 6, wherein the distal end of the elongate member extends in a circle segment, wherein the step of contacting comprises adjusting the diameter of the circle segment to the surface of the cardiac tissue.

8. The method according to claim 1, wherein the curved distal end of the elongate member extends in a plane with respect to an axis of the elongate member, and wherein the step of contacting comprises adjusting the plane to extend the curved distal end to a surface of the cardiac tissue.

9. The method according to claim 1, wherein the catheter comprises a sheath, wherein advancing the catheter through vasculature comprises advancing the catheter through the sheath, wherein the elongate member is moveable between a first position wherein the elongate member extends substantially rectilinear and a second position wherein the distal end of the elongate member is curved, wherein the elongate member moves from the first to the second position by advancing the elongate member out of the sheath.

10. The method according to claim 1, wherein applying the high energy electrical shock comprises using an electrode provided on the catheter as an indifferent electrode.

11. The method according to claim 1, wherein the cardiac tissue comprises pulmonary vein ostia of a pulmonary vein near an entrance to a left atrium.

12. The method according to claim 11, wherein contacting the distal end with the cardiac tissue comprises contacting the ostia of the pulmonary vein with the distal end along a cross section of the pulmonary vein and wherein the high energy electrical shock is applied radially outward from the distal end of the ablation catheter along a cross-section of the pulmonary vein.

13. The method according to claim 12, wherein advancing the ablation catheter to the cardiac tissue comprises advancing a sheath provided with a coil as indifferent electrode in the vicinity of the distal end extending in said left atrium.

14. The method according to claim 1, wherein the step of applying the high energy electrical shock comprises applying a shock between 250 and 400 Joule.

15. The method according to claim 14, wherein the step of applying a high energy electrical shock comprises applying a shock of 350 Joule.

16. The method according to claim 1, wherein the predetermined period of time is less than 5 ms.

17. The method according to claim 16, wherein the predetermined period of time is approximately 1 ms.

18. The method according to claim 1, wherein advancing the ablation catheter to the cardiac tissue comprises inserting the distal end of the ablation catheter into a pulmonary vein.

19. The method according to claim 1, wherein contacting the distal end with the cardiac tissue comprises radially expanding a circle segment of the distal end of the ablation catheter inside a pulmonary vein.

* * * * *